(12) United States Patent
Amarasinghe

(10) Patent No.: US 9,492,627 B2
(45) Date of Patent: Nov. 15, 2016

(54) HEADGEAR ASSEMBLY FOR PATIENT INTERFACE

(75) Inventor: Amal Shirley Amarasinghe, West Pennant Hills (AU)

(73) Assignee: RESMED LIMITED, Bella Vista (AU)

( * ) Notice: Subject to any disclaimer, the term of this patent is extended or adjusted under 35 U.S.C. 154(b) by 2182 days.

(21) Appl. No.: 11/794,151

(22) PCT Filed: Dec. 22, 2005

(86) PCT No.: PCT/AU2005/001940
§ 371 (c)(1),
(2), (4) Date: Jun. 26, 2007

(87) PCT Pub. No.: WO2006/072128
PCT Pub. Date: Jul. 13, 2006

(65) Prior Publication Data
US 2008/0110466 A1    May 15, 2008

Related U.S. Application Data

(60) Provisional application No. 60/640,227, filed on Jan. 3, 2005.

(51) Int. Cl.
*A61M 16/06* (2006.01)

(52) U.S. Cl.
CPC ................................ *A61M 16/0683* (2013.01)

(58) Field of Classification Search
USPC ............ 128/200.24, 201.22–201.24, 202.27, 128/203.29, 205.25, 206.12, 206.14, 128/206.18, 206.21, 206.24, 128/207.11–207.13, 207.17, 848
See application file for complete search history.

(56) References Cited

U.S. PATENT DOCUMENTS

| | | | |
|---|---|---|---|
| 6,119,693 A * | 9/2000 | Kwok et al. | 128/207.11 |
| 2003/0051732 A1* | 3/2003 | Smith et al. | 128/206.27 |
| 2004/0067333 A1 | 4/2004 | Amarasinghe | |
| 2004/0112377 A1 | 6/2004 | Amarasinghe | |

(Continued)

FOREIGN PATENT DOCUMENTS

| | | |
|---|---|---|
| AU | 715075 | 1/2000 |
| DE | 19947722 | 4/2001 |

(Continued)

OTHER PUBLICATIONS

Supplementary European Search Report for corresponding European Application No. 05818571, mailed Jan. 19, 2010, 7 pages.

(Continued)

*Primary Examiner* — Rachel Young
(74) *Attorney, Agent, or Firm* — Nixon & Vanderhye, P.C.

(57) ABSTRACT

A headgear assembly for attachment to a patient interface that delivers breathable gas to a patient, includes a pair of side portions and a rear portion that interconnects the pair of side portions, each of the side portions including an upper side strap and a lower side strap, the rear portion including an upper strap, a lower strap, and intermediate connecting straps extending between the upper strap and the lower strap. The headgear assembly is designed and configured so as to be used with a plurality of different mask systems, and to accommodate for variations in the anthropometrics across a wide variety of patients.

18 Claims, 4 Drawing Sheets

(56) References Cited

U.S. PATENT DOCUMENTS

2004/0221850 A1* 11/2004 Ging et al. ............... 128/206.27
2005/0051178 A1* 3/2005 Sawford ...................... 128/848
2007/0175480 A1* 8/2007 Gradon et al. ........... 128/207.11

FOREIGN PATENT DOCUMENTS

| DE | 10254399 | 6/2004 |
|---|---|---|
| EP | 958841 | 11/1999 |
| EP | 1 020 201 A2 | 7/2000 |
| WO | 0247749 | 6/2002 |
| WO | 2005046776 | 5/2005 |

OTHER PUBLICATIONS

Written Opinion of the International Searching Authority for PCT/AU2005/001940 mailed Mar. 9, 2006.

* cited by examiner

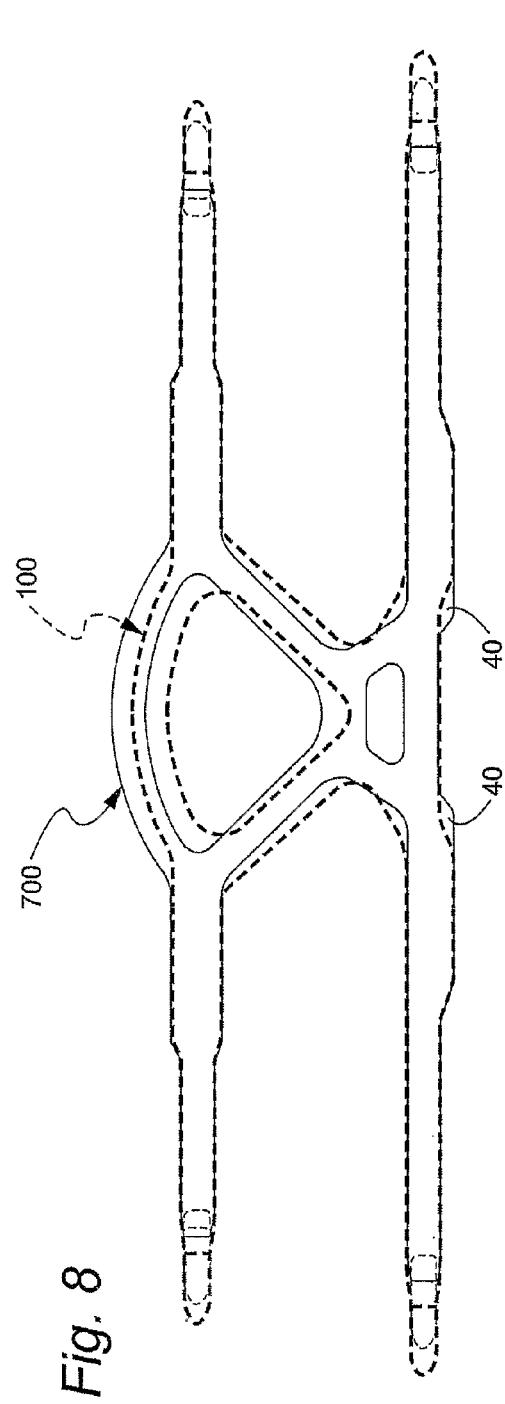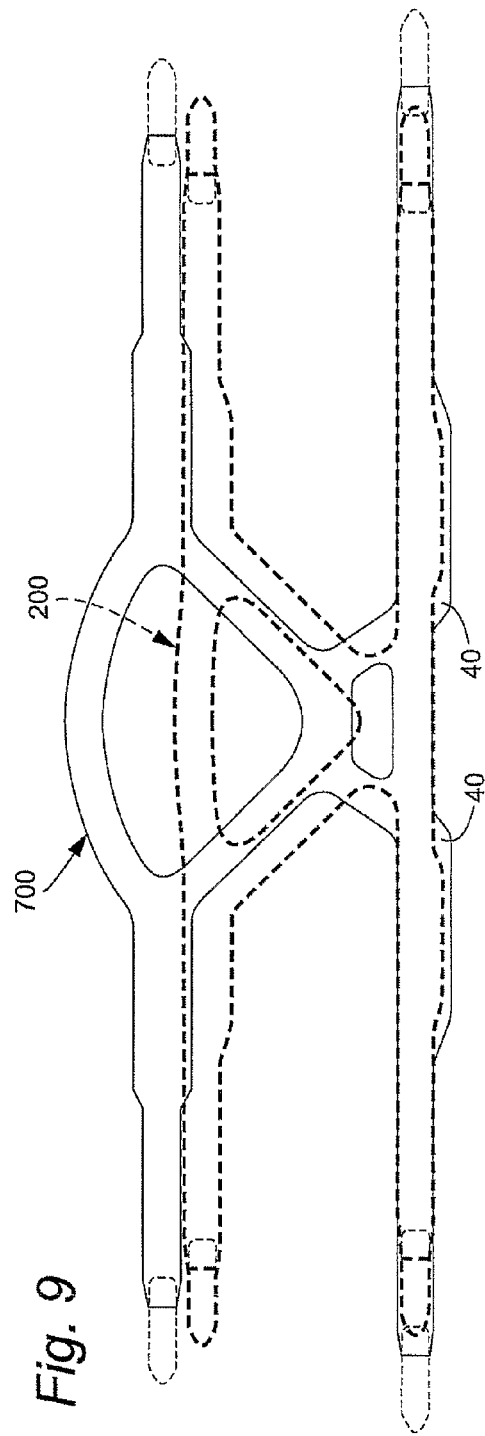

HEADGEAR ASSEMBLY FOR PATIENT INTERFACE

CROSS-REFERENCE TO PRIORITY APPLICATION

This application is the U.S. national phase of international application PCT/AU2005/001940 and claims the benefit of U.S. Provisional Application No. 60/640,227, filed Jan. 3, 2005, each incorporated herein by reference in its entirety.

FIELD OF THE INVENTION

The present invention relates to a headgear assembly for use in holding a patient interface in position on a patient's face, the patient interface being used in the treatment, e.g., of Sleep Disordered Breathing (SDB) with Non-Invasive Positive Pressure Ventilation (NIPPV).

BACKGROUND OF THE INVENTION

Respiratory mask assemblies such as the Mirage® nasal mask assembly manufactured by RedMed Ltd. and used for treatment of SDB such as Obstructive Sleep Apnea (OSA) are typically held in position on a patient's head by a headgear assembly. A headgear assembly typically includes a pair of side portions and a rear portion. The side portions are adapted to engage with the patient's mask and the rear portion is adapted to engage the back of the patient's head.

Headgear assemblies are structured to position and stabilize a patient interface, such as a nasal mask, on a patient's face so that a good seal can be maintained. In addition, the headgear assembly should be comfortable so that a patient can wear the mask assembly at night while they sleep. Many prior art headgear assemblies are uncomfortable to wear for long periods.

For reasons of costs, it is desirable to be able to cut headgear assemblies from a flat piece of fabric or composite, yet in use the headgear assembly should conform to a complex three-dimensional shape. Hence a problem to overcome is to have a design of headgear assembly which can be easily manufactured by cutting or stamping, and yet in use be able to fit a wide range of head shapes and sizes.

A given headgear strap is typically held in position using hook and loop material, for example VELCRO®, by passing an end of the strap through a loop on the mask and then folding it back onto itself. In this way, the strap can be somewhat adjusted to suit the particular needs of the patient in order that a comfortable effective mask seal be effected.

The size and shape of a headgear assembly affect how well it fits a patient. If headgear straps are too short they cannot be used to secure a mask on a large head. If headgear straps are too long they have too much excess material when used on a small head. Similarly if the headgear assembly is the wrong shape then it will not secure the mask in position.

A problem with prior art headgear assemblies is that they do not effectively cover the broadest possible range of patients and thus there are some patients unable to find suitable standard headgear assemblies.

For example, a known headgear assembly 700, commercially sold under the name of Activa® by ResMed Ltd., is illustrated in FIGS. 1-3. Further details of this headgear assembly are disclosed in U.S. patent application Ser. No. 10/655,602, filed Sep. 5, 2003, the entirety of which is hereby incorporated herein by reference.

As illustrated in FIG. 1, the headgear 700 includes a pair of top straps 702, a pair of bottom straps 704 and a rear portion 708. The rear portion 708 is shaped generally like an isosceles triangle with the base 709 of the triangle being arc-like and associated with the top straps 702. A tab 703 with hook & loop material is secured to an end of each of the straps 702 and 704, as shown in FIGS. 1 and 2.

In the illustrated embodiment, the top straps 702 have a length of 610 mm and the bottom straps 704 have a length of 660 mm. These lengths are measured without including the tabs 703 and with the headgear 700 laid flat in an unstretched state. Having a strap of a suitable length means that there is sufficient strap to pass through the connection portion of a mask (not shown) and then fold back so that the hook and loop material on each tab 703 can find sufficient region of the headgear assembly with which to engage.

Each of the straps 702, 704 has a standard width portion 705 and a widened portion 706. In the illustrated embodiment, the height of the headgear assembly 700 is 148 mm. This height is measured from the top of the top straps 702 to the bottom of the bottom straps 704 in the standard width portion 705. Also, the headgear assembly 700 has a height of 196 mm from the bottom of the bottom strap 704 to the top 709b of the arc-like base portion 709. This height dimension contributes to ensuring that a sufficient portion of the crown of the patients head is clasped by the headgear assembly 700.

The headgear assembly 700 is structured for use with one mask embodiment, and provides dimensions (exemplified above) that may not effectively cover the broadest possible range of patients, including patients that have head dimensions that are larger than or smaller than the average patient.

While headgear assemblies can be customized to suit individuals, customized articles tend to be more expensive than mass-produced ones, in the same way that visiting a bespoke tailor might produce better fitting clothes at greater expense. Furthermore, the process of customized fitting (for example cutting up or extending a given headgear assembly) can take time. Thus, it is generally desirable to have standard headgear assembly which fit the broadest range of patients.

SUMMARY OF THE INVENTION

One aspect of the invention is to provide a comfortable headgear assembly for a patient interface which fits a wide range of head shapes and sizes.

Another aspect of the invention relates to a headgear assembly for attachment to a patient interface that delivers breathable gas to a patient. The headgear assembly includes a pair of side portions and a rear portion that interconnects the pair of side portions. Each of the side portions includes an upper side strap and a lower side strap, and the rear portion includes an upper strap, a lower strap, and intermediate connecting straps extending between the upper strap and the lower strap. A height from a bottom of the lower strap of the rear portion to a top of the upper strap of the rear portion is less than about 175 mm.

The height may be in the range of 148-175 mm. In an embodiment, the height may be about 132 mm. An overall length of the upper side straps and the upper strap may be in the range of 610-660 mm, and an overall length of the lower side straps and the lower strap may be in the range of 610-700 mm. In an embodiment, the overall length of the upper side straps and the upper strap may be about 630 mm, and the overall length of the lower side straps and the lower strap may be about 690 mm. An overall length of the upper side straps and the upper strap may be in the range of 530-610 mm, and an overall length of the lower side straps and the lower strap may be in the range of 520-600 mm. In an embodiment, the overall length of the upper side straps and the upper strap may be about 570 mm, and the overall length of the lower side straps and the lower strap may be about 560 mm.

The upper strap, the lower strap, and the intermediate connecting straps may form an opening therebetween. A height from an apex of the opening to the bottom of the lower strap may be less than about 66 mm. In an embodiment, the height from the apex of the opening to the bottom of the lower strap may be about 51 mm. In another embodiment, the height from the apex of the opening to the bottom of the lower strap may be about 38 mm.

A height from a top of the upper side strap to a bottom of the lower side strap may be in the range of 100-138 mm. In an embodiment, the height from the top of the upper side strap to the bottom of the lower side strap may be about 128 mm.

The upper strap may be curved. The upper strap may have a radius of curvature less than about 145 mm. In an embodiment, the upper strap may have a radius of curvature of about 141 mm. The upper strap may have a radius of curvature greater than about 170 mm. In an embodiment, the upper strap may have a radius of curvature of about 430 mm.

Yet another aspect of the invention relates to a headgear assembly for attachment to a patient interface that delivers breathable gas to a patient. The headgear assembly includes upper straps attachable to an upper portion of the patient interface and lower straps attachable to a lower portion of the patient interface. The lower straps have an overall length that is shorter than an overall length of the upper straps.

The overall length of the lower straps may be in the range of 520-600 mm, and the overall length of the upper straps may be in the range of 530-610 mm. In an embodiment, the overall length of the lower straps may be about 560 mm, and the overall length of the upper straps may be about 570 mm.

Yet another aspect of the invention relates to a method of designing a series of breathing arrangements for delivering breathable gas to a patient. The method includes providing at least first and second patient interfaces that are different from one another in at least one aspect, and providing a common headgear assembly that is connectable with each of the first and second patient interfaces.

The method may further include providing third and fourth patient interfaces. At least one of the patient interfaces may be a full-face mask. At least one of the patient interfaces may be a nasal mask. Also, at least one of the patient interfaces may be nasal prongs.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 8 is a top view of the headgear assembly shown in FIG. 4 (in dashed lines) overlaid with the headgear assembly shown in FIG. 1 (in solid tines); and FIG. 9 is a top view of the headgear assembly shown in FIG. 6 (in dashed lines) overlaid with the headgear assembly shown in FIG. 1 (in solid lines).

DETAILED DESCRIPTION OF ILLUSTRATED EMBODIMENTS

FIGS. 4-7 illustrate headgear assemblies 100, 200 constructed according to embodiments of the present invention. Each headgear assembly 100, 200 is adapted to be removably attached to a patient interface structured to deliver breathable gas to a patient. Each headgear assembly 100, 200 maintains the patient interface in a desired position on the patient's face. The patient interface may have any suitable breathing arrangement, e.g., nasal, mouth, nasal and mouth, full-face.

The headgear assemblies 100, 200, also referred to as "common" headgear, are structured such that they may be used with differently shaped and/or sized patient interfaces. Moreover, the headgear assemblies 100, 200 provide two sizes, e.g., large and small, to accommodate a wide range of patient head shapes and sizes. The sizes may be determined from anthropometric data. However, more than two sizes, e.g., small, medium, and large, may be provided. Thus, the headgear assemblies 100, 200 are structured to better and more comfortably fit the patient population.

Figure 3:
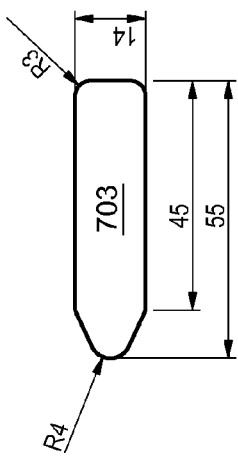
FIGS. 1-3 are top views of a known headgear assembly, commercially sold under the name of Activa® by ResMed Ltd., laid flat and showing typical dimensions of an embodiment.
Figure 2:
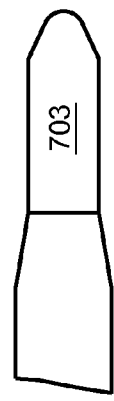
Figure 1:
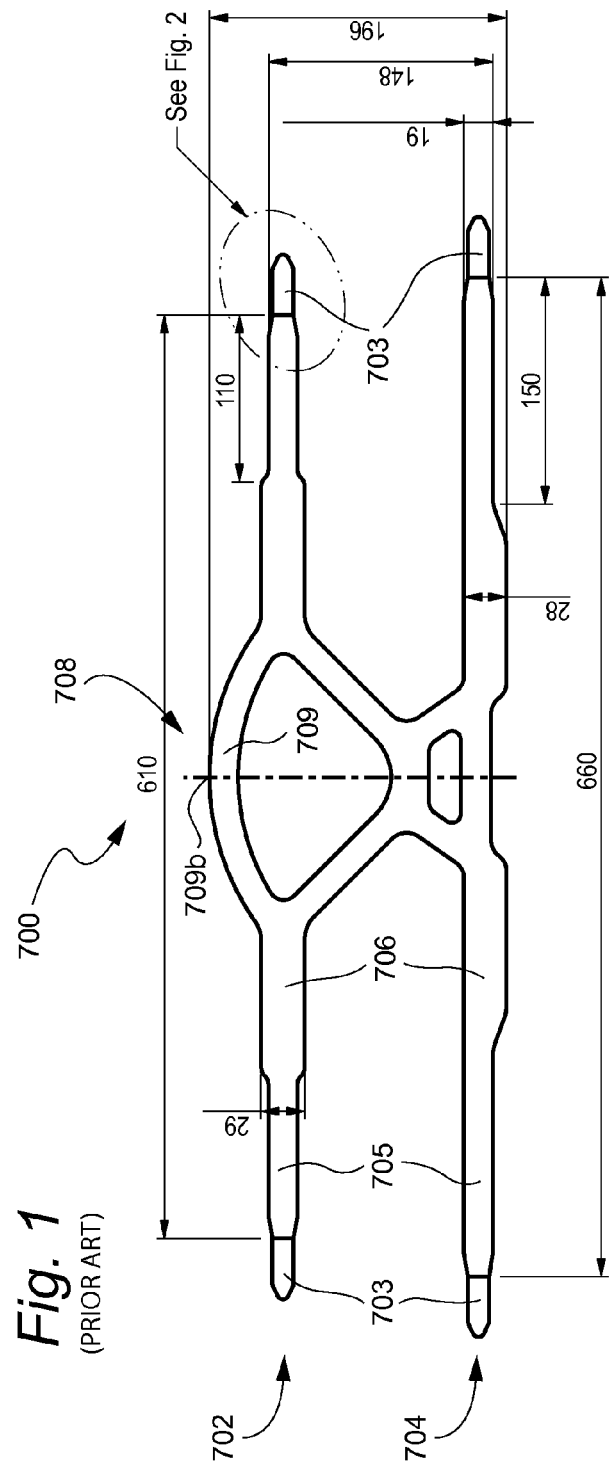
Figure 5:
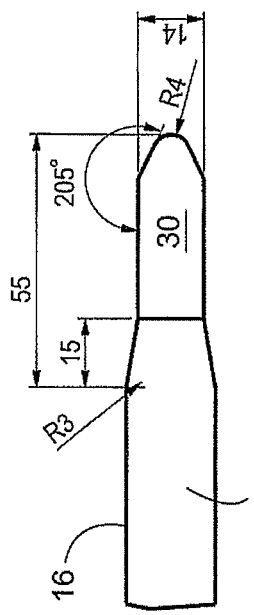
FIGS. 4-5 are top views of a headgear assembly constructed according to an embodiment of the present invention laid flat and showing typical dimensions of an embodiment.
Figure 4:
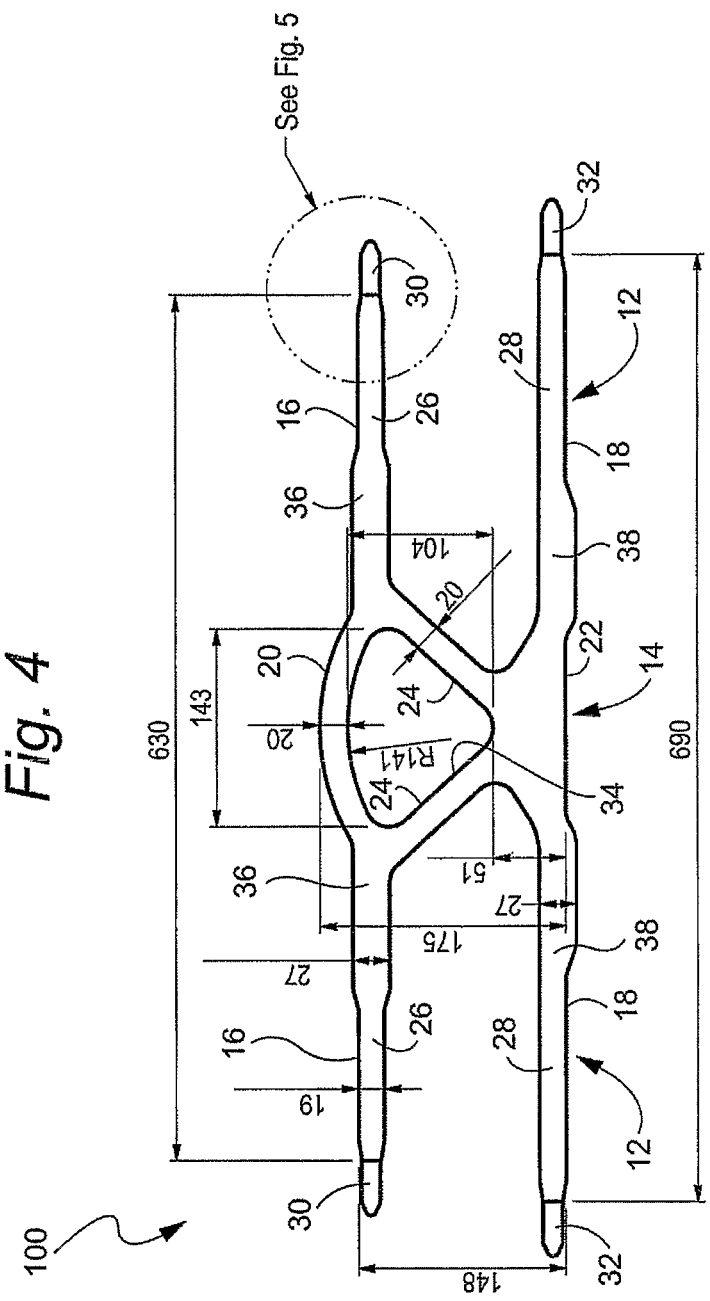
Figure 7:
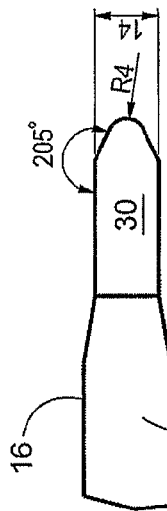
FIGS. 6-7 are top views of a headgear assembly constructed according to another embodiment of the present invention laid flat and showing typical dimensions of an embodiment.
Figure 6:
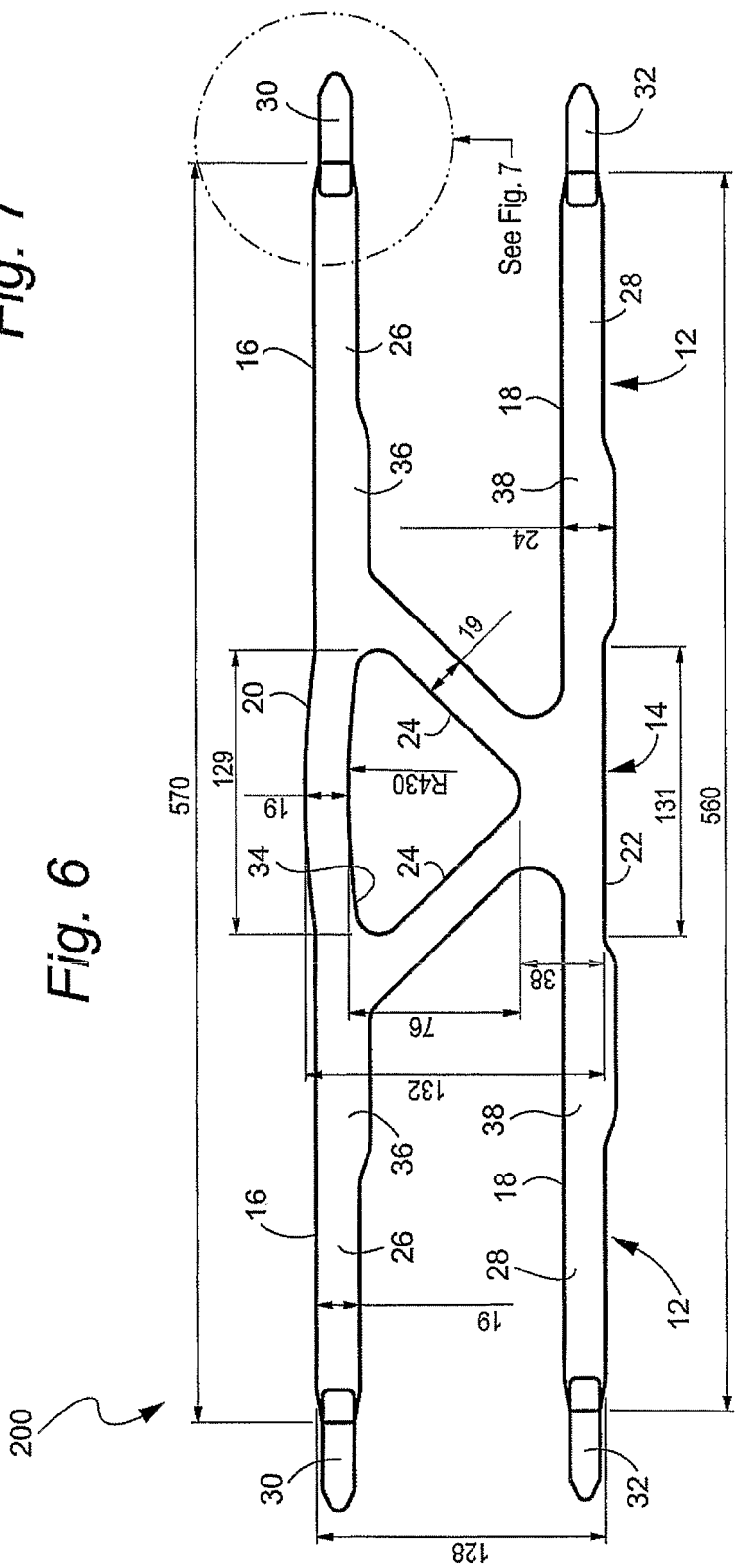

FIGS. 4 and 5 illustrate an embodiment of a "large" headgear assembly 100, and FIGS. 6 and 7 illustrate an embodiment of a "small" headgear assembly 200. The headgear assemblies 100, 200 include substantially similar strap arrangements, but differ in the dimensions of the various strap portions, e.g., length, width, height, radius, etc. The large headgear assembly 100 is structured to provide a good fit on patient's having relatively large heads (e.g., males), and the small headgear assembly 200 is structured to provide a good fit on patient's having relatively small heads (e.g., females and children). Also, the small headgear assembly 200 not only has smaller dimensions with respect to the large headgear assembly 100, it has different proportions or shape with respect to the large headgear assembly 100 to improve fit and comfort.

As noted above, the large and small headgear assemblies 100, 200 include substantially similar strap arrangements which are indicated with similar reference numerals in the figures. As illustrated, each of the headgear assemblies 100, 200 includes two side portions 12 with a rear portion 14 connecting the side portions 12. Each side portion 12 comprises an upper side strap 16 and a lower side strap 18. The rear portion 14, which interconnects the two side portions 12, includes a curved upper strap 20, a lower strap 22, and intermediate connecting straps 24 extending between the curved upper strap 20 and the lower strap 22. The connecting straps 24 are inclined with respect to the curved upper strap 20 and the lower strap 22.

Each upper side strap 16 is removably connectable to an upper portion of the patient interface and each lower side strap 18 is removably connectable to a lower portion of the patient interface. As shown in FIGS. 4 and 6, the end portion 26, 28 of each upper and lower strap 16, 18, respectively, has a reduced width that enables each upper and lower strap 16, 18 to be engaged with a respective connecting structure, e.g., cross-bar, provided on the patient interface. Fastening of the upper and lower straps 16, 18 to the patient interface may be assisted by use of a hook and loop material, such as VELCRO®. As best shown in FIGS. 5 and 7, the free end 30, 32 of each upper and lower strap 16, 18, respectively, includes a strip of hook material attached thereto by stitching, for example. The upper and lower straps 16, 18 are constructed of a loop material that engages the strip of hook material when the upper and lower straps 16, 18 are connected to the patient interface. However, the upper and lower straps 16, 18 may be connected to the patient interface in any other suitable manner, e.g., locking clips.

The straps 16, 18, 20, 22, 24 may be constructed of any suitable material, e.g., flexible material, composite material, etc. Also, one or more of the straps may include a stiffener, such as the stiffener disclosed in U.S. patent application Ser. No. 10/655,602 incorporated herein by reference, to add rigidity to the straps.

In use, the upper side straps 16 extend above the patient's ears, and the lower side straps 18 extend below the patient's ears. The curved upper strap 20 extends across a rear upper portion of the patient's head and the connecting straps 24 and lower strap 22 extend across a rear lower portion of the patient's neck and head.

Further, the straps 20, 22, 24 form an opening 34 therebetween that can accommodate any skin folds of a patient which may extend through the opening 34. In the illustrated embodiment, the opening 34 has a generally triangular shape.

FIGS. 4 and 5 illustrate dimensions of an embodiment of the large headgear assembly 100. For example, the overall length of the upper straps 16, 20 of the large headgear assembly 100 (not including the free ends 30) is in the range of 610-660 mm, preferably 630 mm. The overall length of the lower straps 18, 22 of the large headgear assembly 100 (not including the free ends 32) is in the range of 610-700 mm, preferably 690 mm. Thus, the large headgear assembly 100 is arranged such that the lower straps 18, 22 are longer than the upper straps 16, 20.

Also, the upper straps 16, 20 of the large headgear assembly 100 are about 103% of the length of the corresponding straps of the Activa® headgear assembly 700, and the lower straps 18, 22 of the large headgear assembly 100 are about 105% of the length of the corresponding straps of the Activa® headgear assembly 700. The longer upper and lower straps 16, 18, 20, 22 better accommodate large heads in a broad range of mask user groups.

The large headgear assembly 100 has a height in the range of 130-158 mm, preferably 148 mm, measured from the top of the reduced width portion 26 of the upper strap 16 to the bottom of the reduced width portion 28 of the lower strap 18. Thus, this height of the large headgear assembly 100 is about the same as the corresponding height of the Activa® headgear assembly 700, yet it suitably fits patients with larger head sizes.

The large headgear assembly 100 has a height in the range of 148-186 mm, preferably 175 mm, from the bottom of the lower strap 22 (measured in the reduced width area) to the top of the curved upper strap 20. Thus, this height of the large headgear assembly 100 is about 94% of the corresponding height of the Activa® headgear assembly 700.

The large headgear assembly 100 has a height of about 51 mm from the apex of the opening 34 to the bottom of the lower strap 22 (measured in the reduced width area). The corresponding height of the Activa® headgear assembly 700 is about 66 mm. Thus, this height of the large headgear assembly 100 is shorter than the corresponding height of the Activa® headgear assembly 700, which helps to ease material rolling. The Activa® headgear assembly 700 includes a cut-out window in this area to allow material rolling, whereas the large headgear assembly 100 does not include a cut-out window but provides shorter material height to ease material rolling. Moreover, even without the cut-out window, the large headgear assembly 100 is constructed with less material than the Activa® headgear assembly 700.

The large headgear assembly 100 may include a notch in the apex of the opening 34 to provide additional space for accommodating skin folds of a patient.

FIGS. 4 and 5 illustrate dimensions of an embodiment of the small headgear assembly 200. For example, the overall length of the upper straps 16, 20 of the small headgear assembly 200 (not including the free ends 30) is in the range of 530-610 mm, preferably 570 mm. The overall length of the lower straps 18, 22 of the small headgear assembly 200 (not including the free ends 32) is in the range of 520-600 mm, preferably 560 mm. Thus, the small headgear assembly 200 is arranged such that the lower straps 18, 22 are shorter than the upper straps 16, 20.

This arrangement is in contrast to the Activa® headgear assembly 700 wherein the lower straps are longer than the upper straps. Also, the upper straps 16, 20 of the small headgear assembly 200 are about 93% of the length of the corresponding straps of the Activa® headgear assembly 700, and the lower straps 18, 22 of the small headgear assembly 200 are about 85% of the length of the corresponding straps of the Activa® headgear assembly 700. The shorter upper and lower straps 16, 18, 20, 22 better accommodate small heads in a broad range of mask user groups. For example, the small headgear assembly 200 offers a comfortable strap length to the general female population.

The small headgear assembly 200 has a height in the range of 100-138 mm, preferably 128 mm, measured from the top of the reduced width portion 26 of the upper strap 16 to the bottom of the reduced width portion 28 of the lower strap 18. Thus, this height of the small headgear assembly 200 about 86% of the corresponding height of the Activa® headgear assembly 700.

The small headgear assembly 200 has a height of about 132 mm, from the bottom of the lower strap 22 (measured in the reduced width area) to the top of the curved upper strap 20. This height is substantially shorter than the corresponding heights of the Activa® headgear assembly 700. For example, this height of the small headgear assembly 200 is about 71% of the corresponding height of the Activa® headgear assembly 700. The shorter height of the small headgear assembly 200 provides a better and more comfortable fit for patients with smaller head shapes and sizes, e.g., the female population.

The small headgear assembly 200 has a height of about 38 mm from the apex of the opening 34 to the bottom of the lower strap 22 (measured in the reduced width area). The corresponding height of the Activa® headgear assembly 700 is about 66 mm. Thus, this height of the small headgear assembly 200 is shorter than the corresponding height of the Activa® headgear assembly 700, which helps to ease material rolling.

As illustrated, the triangular opening 34 of the small headgear assembly 200 is smaller than the corresponding opening of both the large headgear assembly 100 and the Activa® headgear assembly 700. For example, the opening 34 of the small headgear assembly 200 has a height of about 76 mm and a width of about 129 mm, whereas the opening 34 of the large headgear assembly 100 has a height of about 104 mm and a width of about 143 mm. This smaller opening also provides a better and more comfortable fit for patients with smaller head shapes and sizes, e.g., the female population.

Also, the curved upper strap 20 of the large headgear assembly 100 has a radius of curvature of about 141 mm, and the curved upper strap 20 of the small headgear assembly 200 has a radius of curvature of about 430 mm. Thus, the curved upper strap 20 of the small headgear assembly 200 is flatter than the curved upper strap 20 of the large headgear assembly 100 to better accommodate patients with smaller head shapes and sizes.

Further, strap widths of the small headgear assembly 100 are smaller than strap widths of the large headgear assembly 200. For example, the curved upper strap 20 of the small headgear assembly 200 has a width of about 19 mm, whereas the curved upper strap 20 of the large headgear assembly 100 has a width of about 20 mm. The connecting straps 24 of the small headgear assembly 200 have a width of about 19 mm, whereas the connecting straps 24 of the large headgear assembly 100 have a width of about 20 mm. Also, the enlarged width portion 36, 38 of the upper and lower straps 16, 18, respectively, of the small headgear assembly 200 have a width of about 24 mm, whereas the corresponding portions of the large headgear assembly 100 have a width of about 27 mm. The smaller width straps of the small headgear assembly 200 help to reduce the bulkiness of the headgear assembly as well as improve comfort.

FIGS. 8 and 9 show the large and small headgear assemblies 100, 200 in relation to the Activa® headgear assembly 700. As shown in FIG. 8, the large headgear assembly 100 has upper and lower straps 16, 18, 20, 22 that are longer, the height from the bottom of the lower strap 22 (measured in the reduced width area) to the top of the curved upper strap 20 is shorter, and the height from the apex of the opening 34 to the bottom of the lower strap 22 (measured in the reduced width area) is shorter. Additionally, the opening 34 is smaller and dips down further. This size of the large headgear assembly 100 provides a better and more comfortable fit for patients with larger heads.

As shown in FIG. 9, the small headgear assembly 200 has upper and lower straps 16, 18, 20, 22 that are shorter, the height from the top of the reduced width portion 26 of the upper strap 16 to the bottom of the reduced width portion 28 of the lower strap 18 is shorter, the height from the bottom of the lower strap 22 (measured in the reduced width area) to the top of the curved upper strap 20 is shorter, and the height from the apex of the opening 34 to the bottom of the lower strap 22 (measured in the reduced width area) is shorter. Additionally, the small headgear assembly 200 has lower straps 18, 22 that are shorter than the upper straps 16, 20, which is counterintuitive to known headgear assemblies such as the Activa® headgear assembly 700.

Further, as shown in FIGS. 8 and 9, lower strap portions 40 of both the large headgear assembly 100 and the small headgear assembly 200 are removed (with respect to the Activa® headgear assembly 700) to improve fit and comfort.

Whilst the invention has been described in terms of preferred embodiments, it would be possible to make a single adjustable headgear assembly to suit the range of sizes offered by the preferred embodiments. Such headgear assembly would have adjustable straps and an adjustable triangular opening at the back. These adjustments may be achieved, e.g., via stitching/unstitching straps, by the use of dress-making hooks, Velcro® or similar fasteners, adding buttons, etc. Such adjustments would preferably provide for a range of head sizes offered by the preferred embodiment. For example, the bottom straps would be adjustable from about 560 mm to 690 mm.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

The invention claimed is:

1. A headgear assembly for attachment to a patient interface that delivers breathable gas to a patient, including: a pair of side portions and a rear portion that interconnects the pair of side portions, each of the side portions including an upper side strap and a lower side strap, the rear portion including an upper strap, a lower strap, and intermediate connecting straps extending between the upper strap and the lower strap, wherein: a height from a bottom of the lower strap of the rear portion to a top of the upper strap of the rear portion is less than about 175 mm.

2. The headgear assembly according to claim 1, wherein the height is in the range of 148-175 mm.

3. The headgear assembly according to claim 1, wherein the height is about 132 mm.

4. The headgear assembly according to claim 1, wherein an overall length of the upper side straps and the upper strap is in the range of 610-660 mm and an overall length of the lower side straps and the lower strap is in the range of 610-700 mm.

5. The headgear assembly according to claim 4, wherein the overall length of the upper side straps and the upper strap is about 630 mm, and the overall length of the lower side straps and the lower strap is about 690 mm.

6. The headgear assembly according to claim 1, wherein an overall length of the upper side straps and the upper strap is in the range of 530-610 mm, and an overall length of the lower side straps and the lower strap is in the range of 520-600 mm.

7. The headgear assembly according to claim 6, wherein the overall length of the upper side straps and the upper strap is about 570 mm, and the overall length of the lower side straps and the lower strap is about 560 mm.

8. The headgear assembly according to claim 1, wherein the upper strap, the lower strap, and the intermediate connecting straps form an opening therebetween.

9. The headgear assembly according to claim 8, wherein a height from an apex of the opening to the bottom of the lower strap is less than about 66 mm.

10. The headgear assembly according to claim 9, wherein the height from the apex of the opening to the bottom of the lower strap is about 51 mm.

11. The headgear assembly according to claim 9, wherein the height from the apex of the opening to the bottom of the lower strap is about 38 mm.

12. The headgear assembly according to claim 1, wherein a height from a top of the upper side strap to a bottom of the lower side strap is in the range of 100-138 mm.

13. The headgear assembly according to claim 12, wherein the height from the top of the upper side strap to the bottom of the lower side strap s about 128 mm.

14. The headgear assembly according to claim 1, wherein the upper strap is curved.

15. The headgear assembly according to claim 14, wherein the upper strap has a radius of curvature less than about 145 mm.

16. The headgear assembly according to claim 15, wherein the upper strap has a radius of curvature of about 141 mm.

17. The headgear assembly according to claim 14, wherein the upper strap has a radius of curvature greater than about 170 mm.

18. The headgear assembly according to claim 17, wherein the upper strap has a radius of curvature of about 430 mm.

* * * * *